United States Patent [19]

Herrera V. et al.

[11] Plant 4,686

[45] Apr. 7, 1981

[54] CHRYSANTHEMUM PLANT

[75] Inventors: Camilo Herrera V.; Reinaldo Saavedra, both of Bogota, Colombia

[73] Assignee: Jardines de Lose Andes Ltda., Bogota, Colombia

[21] Appl. No.: 38,166

[22] Filed: May 11, 1979

[51] Int. Cl.[3] ..... A01H 5/00

[52] U.S. Cl. ..... Plt./76

[58] Field of Search ..... Plt./76, 80–81

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant referred to by the cultivar name Sofia and a sport of the cultivar Deep Telstar, disclosed in U.S. Plant Pat. No. 3,373. Sofia is distinguished from the parent cultivar by its dark lavender ray floret color.

2 Drawing Figures

The present invention comprises a new and distinct cultivar of *Chrysanthemum morifolium,* Ramat., hereinafter referred to by the cultivar name Sofia.

Sofia is a spontaneous mutation of the cultivar Deep Telstar (disclosed in U.S. Plant Pat. No. 3,373) and was selected to expand the color range of the parental variety.

Sofia was discovered and selected by Camilo Herrara V. on Mar. 16, 1976 as one plant within a flowering block of Deep Telstar in Bogota, Colombia. The first act of asexual reproduction of Sofia was accomplished when vegetative cuttings were taken from the initial selection in Bogota, Colombia by Reinaldo Saavedra working under formulations established and supervised by Camilo Herrera V.

Continued asexual reproduction by vegetative cuttings for evaluative flowering tests in conjunction with horticultural examination of selected units initiated Aug. 8, 1978 has demonstrated that the combination of characteristics as herein disclosed for Sofia are firmly fixed and are retained through successive generations of asexual reproduction.

Sofia has not been observed under all possible enviromental conditions. The phenotype may vary significantly with variations in environment such as temperature, light intensity and daylength. The following observations, measurements and comparisons describe plants grown in Bogota, Colombia under environmental conditions which approximate those generally used in commercial practice.

The following traits have been repeatedly observed and are determined to be basic characteristics of Sofia which in combination distinguish this chrysanthemum as a new and distinct cultivar:

(1) Decorative capitulum type;

(2) Flat capitulum form, reflexing at maturity;

(3) Dark lavender ray floret color;

(4) Diameter across face of inflorescence ranging from 95 to 125 mm at maturity;

(5) Uniform eleven week photoperiodic flowering response to short days;

(6) Tall plant height (requires 1–2 long day weeks prior to short days to attain a flowered plant height of 77 to 82 cm when grown as a single stem plant for April through November flowerings); and (7) Semi-upright branching pattern.

The accompanying color photographic drawing shows typical inflorescence and foliage characteristics of Sofia, with the colors being as nearly true as possible with photographic drawings of this type. Sheet 1 is a color photograph of the inflorescence of Sofia. Sheet 2 is a black and white photograph showing Sofia as a cut spray.

Of the many commercial cultivars known to the present inventors the most similar in comparison to Sofia is the parental cultivar Deep Telstar. Reference is made to attached Chart A which compares certain characteristics of Sofia with the same characteristics of Deep Telstar. It will be noted that Sofia has a different ray floret color, being dark lavender. Other characteristics of Sofia are similar to those same characteristics of Deep Telstar.

In the following description, color references are made to The Royal Horticultural Society Colour Chart. The color values were determined between 4:30 and 5:00 P.M. on Mar. 20, 1979 under 100 foot-candle light intensity at Salinas, Calif.

Classification:

*Botanical.*—*Chrysanthemum morifolium,* Ramat., cv Sofia.

*Commercial.*—Cut decorative spray.

I. Inflorescence:

A. *Capitulum.*—Form: Flat. Type: Decorative. Permanence: 14 to 18 days. Diameter across face: 95 to 125 mm.

B. *Corolla of ray florets.*—Form: Flat, with pronounced longitudinal roll when immature. Color (abaxial): 70-B. Color (adaxial): 70-B streaked lightly over 69-B. General color tonality from a distance of three meters: 70-B to 70-C streaked over 69-B.

C. *Reproductive organs.*—Androecium: none. Gynoecium: present both ray and disc florets.

II. Plant:

A. *General appearance.*—Semi-upright branching pattern; tall height.

B. *Foliage.*—Color (abaxial): 137-A. Color (adaxial): 137-C.

CHART A

COMPARISON OF SOFIA AND DEEP TELSTAR

| CULTIVAR | RAY FLORET COLOR | DIAMETER ACROSS FACE OF CAPITULUM | PLANT HEIGHT |
|---|---|---|---|
| Sofia | Dark | 95 to 125 mm. | Tall, |

CHART A-continued

| COMPARISON OF SOFIA AND DEEP TELSTAR | | | |
|---|---|---|---|
| | Lavender | | 77 to 82 cm. |
| Deep Telstar | Lavender | 95 to 125 mm. | Tall, 77 to 82 cm. |

| CULTIVAR | BRANCHING PATTERN | FLOWERING RESPONSE PERIOD | CAPITULUM FORM AND TYPE |
|---|---|---|---|
| Sofia | Semi-upright | 11 week | Flat Decorative |
| Deep | Semi- | 11 week | Flat |

CHART A-continued

| COMPARISON OF SOFIA AND DEEP TELSTAR | | |
|---|---|---|
| Telstar | upright | Decorative |
| COMPARISONS MADE OF PLANTS GROWN IN BOGOTA, COLUMBIA AS SINGLE STEM CUT SPRAYS. | | |

We claim:

1. A new and distinct cultivar of *Chrysanthemum morifolium;* Ramat., known by the cultivar name Sofia and particularly characterized as to uniqueness by the combined characteristics of decorative capitulum type; flat capitulum form; dark lavender ray floret color; diameter across face of capitulum from 95 to 125 mm at maturity; uniform eleven week response to photoperiodic short-day control; tall plant height; and semi-upright branching pattern.

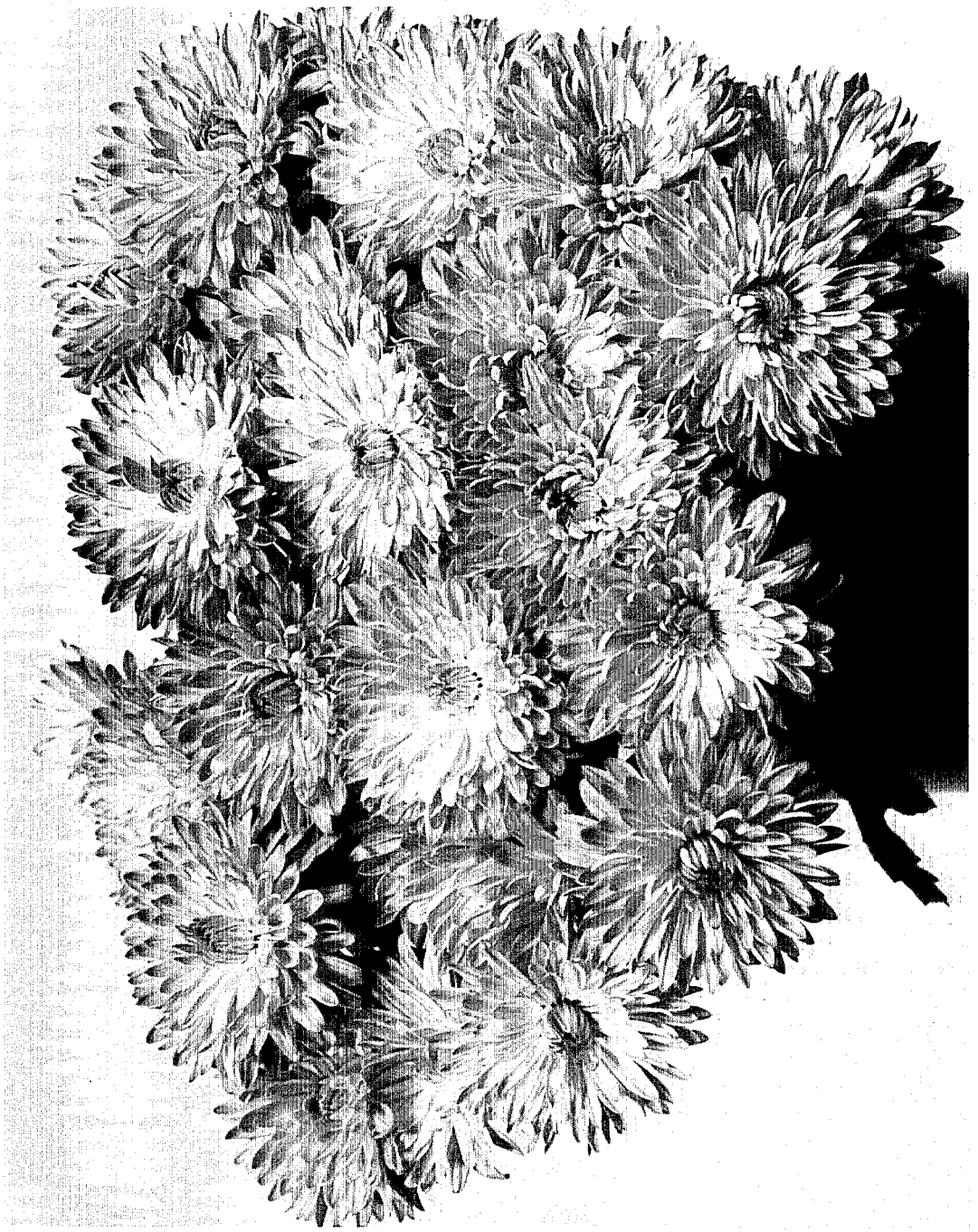

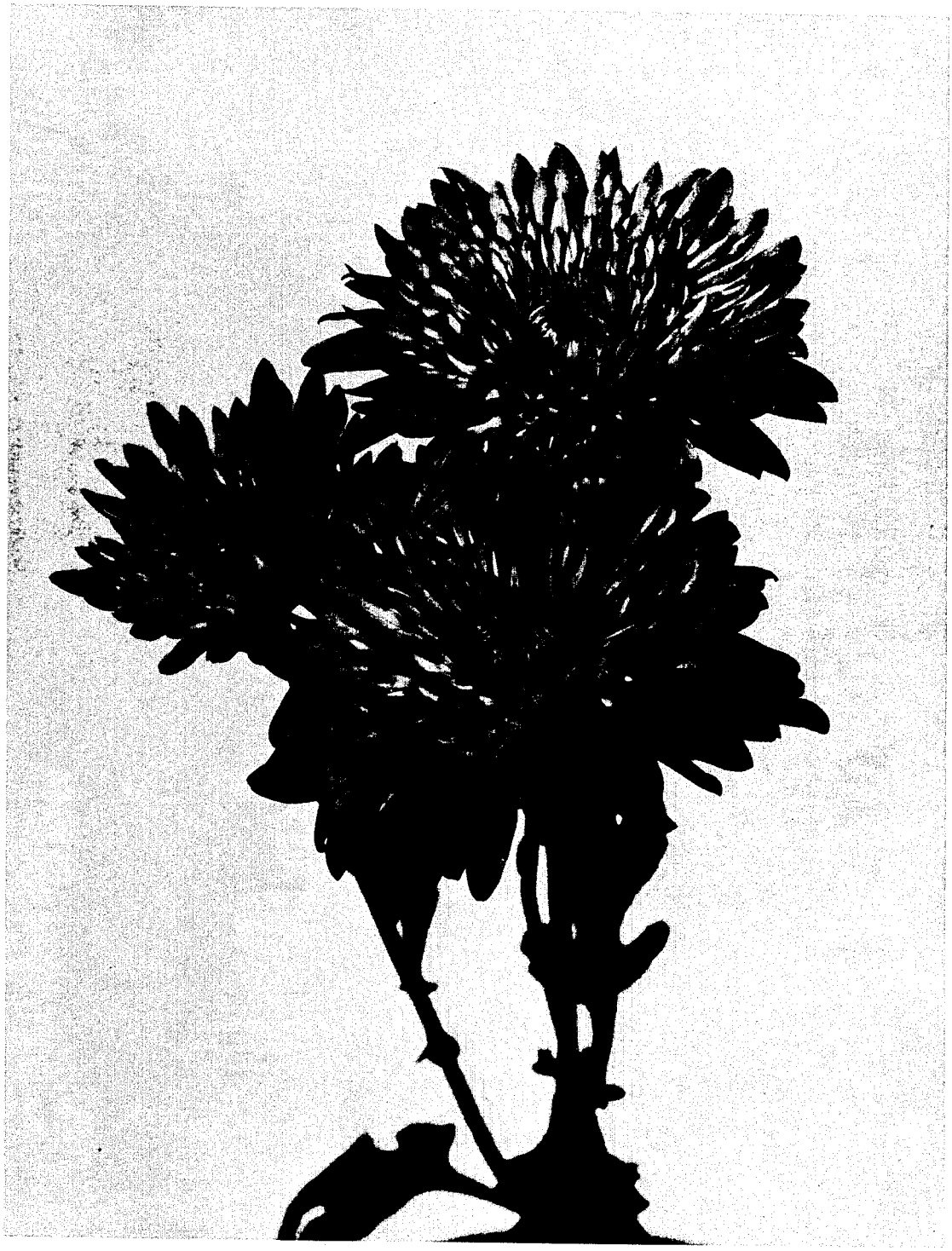

* * * * *